US008146586B2

(12) United States Patent
Kobayashi et al.

(10) Patent No.: US 8,146,586 B2
(45) Date of Patent: Apr. 3, 2012

(54) LIQUID EJECTION CARTRIDGE AND LIQUID EJECTION DEVICE

(75) Inventors: Masaya Kobayashi, Yokohama (JP); Kenichi Sekine, Ageo (JP)

(73) Assignee: Canon Kabushiki Kaisha, Tokyo (JP)

( * ) Notice: Subject to any disclaimer, the term of this patent is extended or adjusted under 35 U.S.C. 154(b) by 1065 days.

(21) Appl. No.: 12/065,702

(22) PCT Filed: Oct. 16, 2006

(86) PCT No.: PCT/JP2006/320976
§ 371 (c)(1), (2), (4) Date: Mar. 4, 2008

(87) PCT Pub. No.: WO2007/046508
PCT Pub. Date: Apr. 26, 2007

(65) Prior Publication Data
US 2009/0165789 A1   Jul. 2, 2009

(30) Foreign Application Priority Data

Oct. 18, 2005  (JP) ................... 2005-303179

(51) Int. Cl.
*A61M 11/00* (2006.01)
*A61M 37/00* (2006.01)
*A61K 9/22* (2006.01)

(52) U.S. Cl. .................. 128/200.14; 604/890.1; 604/82; 604/87

(58) Field of Classification Search ........... 128/200.14–200.23, 203.12, 203.14, 128/203.19–203.21; 604/890.1, 891.1, 82, 604/86, 87; 222/81, 83–88, 94–96, 541.2; 239/102.1, 102.2
See application file for complete search history.

(56) References Cited

U.S. PATENT DOCUMENTS 5,352,196 A * 10/1994 Haber et al. .................. 604/90
5,360,410 A * 11/1994 Wacks .......................... 604/232
6,626,379 B1   9/2003 Ritsche et al.
(Continued)

FOREIGN PATENT DOCUMENTS

JP   05-329192 A1   12/1993
(Continued)

OTHER PUBLICATIONS

Int'l Search Report mailed Nov. 28, 2006, for International Application No. PCT/JP2006/320976.
(Continued)

Primary Examiner — Justine Yu
Assistant Examiner — Rachel Young
(74) Attorney, Agent, or Firm — Fitzpatrick, Cella, Harper & Scinto

(57) ABSTRACT

Provided are a liquid ejection cartridge and a liquid ejection device each having a simple structure capable of surely mixing a plurality of liquids. An example of the liquid ejection cartridge includes a liquid ejection portion (12) for ejecting a liquid; a first liquid storage portion (3) which is separated from the liquid ejection portion (12) through a film (10); a second liquid storage portion (4) which is separated from the first liquid storage portion (3) through a film (9). Further, the liquid ejection cartridge further includes a first penetrating member (8) for penetrating the film (10) which separates the liquid ejection portion (12) and the first liquid storage portion (3); and a second penetrating member (7) for penetrating the film (9) which separates the first liquid storage portion (3) and the second liquid storage portion (4).

8 Claims, 5 Drawing Sheets

U.S. PATENT DOCUMENTS

| | | | |
|---|---|---|---|
| 6,886,557 B2 * | 5/2005 | Childers et al. | 128/200.14 |
| 7,147,172 B2 * | 12/2006 | Darling et al. | 239/302 |
| 2004/0050383 A1 | 3/2004 | Cox et al. | |
| 2004/0107961 A1 * | 6/2004 | Trueba | 128/200.16 |
| 2005/0000514 A1 * | 1/2005 | Sullivan et al. | 128/200.24 |
| 2005/0150489 A1 * | 7/2005 | Dunfield et al. | 128/200.14 |
| 2007/0240706 A1 | 10/2007 | Kobayashi et al. | 128/200.14 |
| 2008/0295827 A1 | 12/2008 | Kobayashi et al. | 128/200.16 |

FOREIGN PATENT DOCUMENTS

| | | |
|---|---|---|
| JP | 11-089934 A1 | 4/1999 |
| JP | 2001010076 A * | 1/2001 |
| JP | 2001161819 A * | 6/2001 |
| JP | 2005-058421 | 3/2005 |
| JP | 2005-081124 | 3/2005 |
| WO | 00/21598 A1 | 4/2000 |
| WO | 99/24170 A1 | 3/2008 |

OTHER PUBLICATIONS

Written Opinion of the International Searching Authority mailed Nov. 28, 2006, for International Application No. PCT/JP2006/320976.

* cited by examiner

LIQUID EJECTION CARTRIDGE AND LIQUID EJECTION DEVICE

This application is a National Stage filing under 35 U.S.C. § 371 of International Application No. PCT/JP2006/320976, filed Oct.16, 2006.

TECHNICAL FIELD

The present invention relates to a liquid ejection cartridge and a liquid ejection device. The liquid ejection cartridge and liquid ejection device according to the present invention are suitably employed as an inhaler used when atomizing a liquid drug and allowing the drug to be inhaled into the body (especially the lungs) in the medical field and the like.

BACKGROUND ART

In recent years, the average life expectancy has been increasing, thereby increasing the elderly population because of advances in medicine and science. However, with changes in dietary habits or living environments and the environmental pollution, and new illnesses and infectious diseases due to viruses or fungi have appeared, so that anxiety about people's health has been increasing. Particularly, in the so-called advanced nations, the increase of patients of life-style related diseases such as diabetes mellitus, hypertension or the like has become a problem.

On the other hand, since the number of medical institutions has not so increased as to cope with such increase of patients, and since there are communities where there is no medical institution which patients can attend, there is a concern for how to cope therewith, also from the viewpoint of public policy.

Description will be made below with reference to a specific example. Of the diabetes mellitus patients who are increasing at present, the so-called insulin-dependent type (type 1) diabetes mellitus patients have no secretion of insulin from their pancreas and need to be regularly administered with insulin. Because insulin is administered by subcutaneous injection at present, the physical and mental inconvenience to patients is large.

In order to reduce the inconvenience of such users, a pen-shaped injection syringe has been developed which has a thin needle and causes less pain to a patient. However, because most type 1 diabetes mellitus patients work as able-bodied persons except for requiring regular administration of insulin, they have a mental resistance to injection in public even with a pen-shaped injection syringe, so that it is difficult to administer insulin at the proper times. As a result, with such a method, there is a possibility that the users may not be treated appropriately.

On the other hand, a treatment for a user in which a drug ejection device for allowing the user to intake the drug through inhalation is utilized in combination with information database such as electronic medical records is being embodied. By applying an ink jet system to an ejection mechanism of such a drug ejection device, it is possible accurately to control the liquid droplet diameter and ejection amount of a liquid drug (see International Publications Nos. WO 95/01137 and WO 02/04043).

In an inhaler used in the medical field when atomizing a liquid drug for pulmonary inhalation, not only a system for administrating a drug of a single kind but also a system suitable for mixing/administrating different kinds of drugs has been required. In this case, different kinds of drugs are mixed/administrated by mixing the drugs and encapsulating the mixture in a tank in advance, as long as the drugs thus prepared do not change over time. However, there are also many drugs which need to be administered within a short time after mixing. In such the case, the drugs need to be mixed immediately before the administration.

Further, there are cases where the amounts or kinds of drugs to be administered need to be varied depending on the condition of a user, so that there has been a demand for a method of preparing an ejection liquid in which the composition of the liquid can be easily and surely changed.

Japanese Patent Application Laid-Open No. H11-010859 discloses an example of a liquid ejection device in which liquids are mixed prior to ejection. However, the liquid ejection device adopts a system in which when liquids contained in a plurality of housing parts are mixed, respective liquids are separately supplied through controlling valves and mixed, and thereafter ejected, which requires a complicated structure, and thus has a problem that the system is not suitable for attaining size reduction.

Because it is preferable that the drug ejection device such as described above is so configured as to be portably carried by the user, it is undesirable that the size of the device is increased due to the provision of a mechanism in which liquids are mixed prior to ejection. In other words, the mechanism of mixing liquids prior to the ejection adopted in the conventional liquid ejection device is not suitable for application in the above-mentioned drug ejection device.

DISCLOSURE OF THE INVENTION

The present invention has been accomplished in order to solve the above- mentioned problems, and it is, therefore, an object of the present invention to provide a liquid ejection cartridge and a liquid ejection device each having a simple structure capable of surely mixing a plurality of liquids.

A liquid ejection cartridge according to the present invention comprises a liquid ejection portion for ejecting a liquid; a first liquid storage portion which is separated from the liquid ejection portion through a film; a second liquid storage portion which is separated from the first liquid storage portion through a film. Further, the liquid ejection cartridge of the present invention further comprises a first penetrating member for penetrating the film which separates the liquid ejection portion and the first liquid storage portion; and a second penetrating member for penetrating the film which separates the first liquid storage portion and the second liquid storage portion.

According to the present invention, because a plurality of containers separately provided can be interpenetrated through the penetrating member, it is possible to easily mix the plurality of liquids within the device. Also, the device has a simple structure and can therefore be manufactured with ease. Further, the device is capable of keeping liquids, for which liquid stability is necessary, and powders separated until immediately before the ejection, and is therefore suitable for a combination of substances that will denature immediately after mixing.

Other features and advantages of the present invention will be apparent from the following description taken in conjunction with the accompanying drawings, in which like reference characters designate the same or similar parts throughout the figures thereof.

BEST MODE FOR CARRYING OUT THE INVENTION

Figure 1:
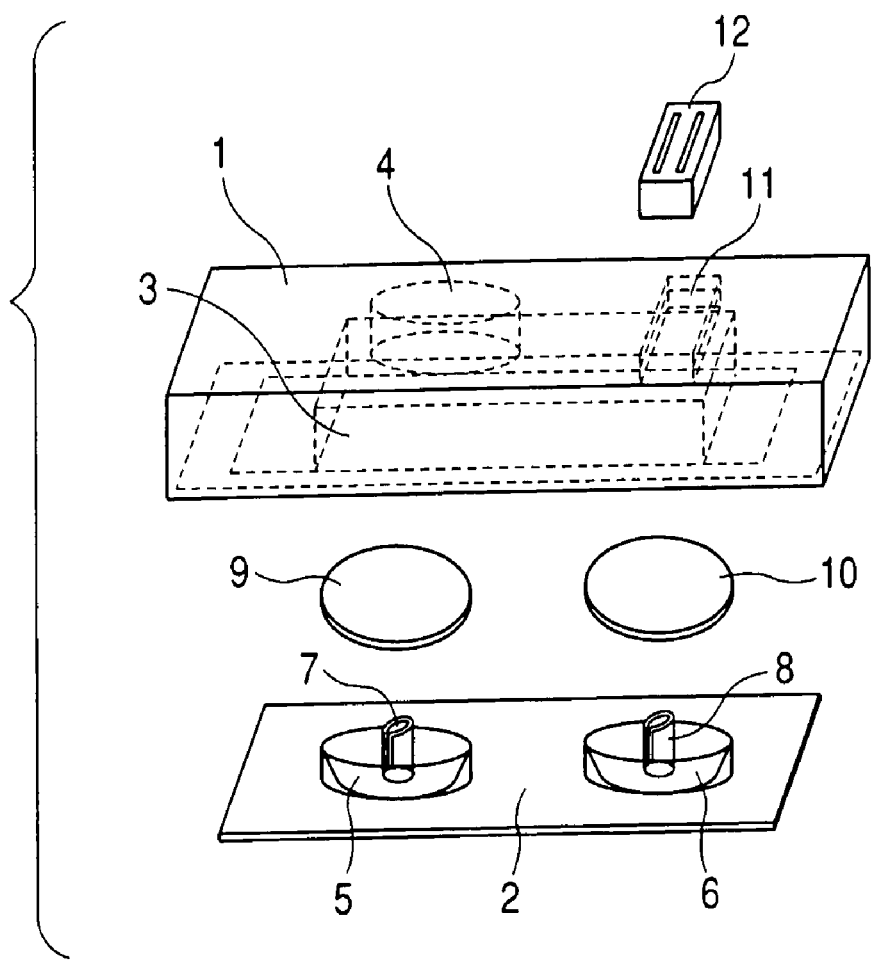
FIG. 1 is an exploded perspective view showing a liquid ejection cartridge according to one embodiment of the present invention.

Preferred embodiments of the present invention will now be described in detail in accordance with the accompanying drawings.

The liquid ejection cartridge of the present invention has a plurality of liquid storage portions separated by a film; and a penetrating member for penetrating the film such that the liquids separately retained in the respective liquid storage portions can be mixed. The mixed liquids (liquid mixture) can be supplied to the liquid ejection portion as long as at least one of the plurality of liquid storage portions is in communication with the liquid ejection portion. According to the structure of the present invention, it is possible to mix various kinds of liquids with a simple structure.

That is, the liquid ejection cartridge of the present invention comprises a liquid ejection portion for ejecting a liquid; a first liquid storage portion which is separated from the liquid ejection portion through a film; a second liquid storage portion which is separated from the first liquid storage portion through a film. Further, the liquid ejection cartridge of the present invention further comprises a first penetrating member for penetrating the film which separates the liquid ejection portion and the first liquid storage portion; and a second penetrating member for penetrating the film which separates the first liquid storage portion and the second liquid storage portion.

Although the structure of the liquid ejection portion is not particularly limited as long as it can eject a liquid in a form of liquid droplets, it is preferable that the liquid ejection portion is an ink jet head utilizing the ink jet technology. In particular, it is preferable to adopt a bubble jet system in which a liquid is heated by using a heater element to cause film boiling, thereby to generate bubbles, and the energy of the bubble formation is utilized for ejecting liquid droplets through a nozzle. The adoption of this system makes it easy to provide a large number of ejection nozzles. Incidentally, as the element for applying ejection energy, a piezoelectric element may also be used.

Alternatively, it is possible to adopt a structure in which a liquid is absorbed in a porous member, and the porous member is vibrated to eject a large number of liquid droplets.

By allowing the first penetrating member to penetrate the film which separates the liquid ejection portion and the first liquid storage portion, the liquid ejection portion and the first liquid storage portion are brought into communicated with each other, thereby causing liquid movement. As a result, the head is filled with the liquid. The means for the communication may be a flow path which is generally used in the ink jet technology, and may not necessarily be established immediately before the ejection operation. However, it is more preferable that the liquid ejection portion and the first liquid storage portion are brought into communication with each other after the first liquid storage portion and the second liquid storage portion have been brought into communication with each other, because the mixed liquids can be supplied to the supply portion.

It is also preferable that the plurality of liquid storage portions are made in a unit. Further, it is preferable to adopt a structure in which the liquid ejection portion is integrated with the liquid storage portion to form a liquid ejection cartridge, which is to be installed for use in a liquid ejection device main body having a controller for controlling the ejection portion and a housing portion. In this case, it is preferable to design the cartridge portion to be disposable from the viewpoint of hygiene.

It is preferable that each of the plurality of the liquid storage portions is made of a material having less influence on living body when used for medical purposes, and there can be used a single component resin such as polyethylene, flexible polypropylene, polycarbonate, ABS resin, or methacrylate resin; or composite plastics such as polyethylene/eval (trade name of ethylene vinyl alcohol copolymer; manufactured by KURARAY CO., LTD.).

The liquid or solid to be contained in each of the plurality of liquid storage portions is selected suitably depending on the purpose thereof.

For example, the first liquid storage portion may contain a composition for ejection so adjusted in viscosity and surface tension as to provide a suitable ejection performance when ejecting a liquid, while the second liquid storage portion may contain a liquid drug (and further, the third and subsequent liquid storage portions each may contain a liquid drug). Adoption of a structure such that plural kinds of liquids are separately contained and stored without being mixed until immediately before use is suitable for a mixing system for drugs that will denature immediately due to mixing, and for a system capable of appropriately adjusting the amounts of drugs.

Further, the liquids contained in the respective liquid storage portions all may have the same composition. In such the case, the liquids may be different in concentration so as to be suitably used for changing the concentrations depending on use conditions.

The operation for bringing the first and the second liquid storage portions, which have been separated until the mixing, is not particularly limited as long as the liquids are allowed to move after the communication such that a liquid or a solid (or a powder) stored in each of the storage portions can be surely subjected to mixing. Examples of the structure performing such operation include a simple structure in which a film for separating the two liquid storage portions and a penetrating member for penetrating the film are provided in the storage portions, and the penetrating member is allowed to penetrate the separating film in use to form a penetrated opening.

In order that the two storage portions sufficiently communicate with each other, it is preferable to provide the penetrating member with an uneven structure such as groove, which enables the liquids to move even in the state in which the penetrating member penetrates the film. When using a penetrating member having no groove formed therein, the penetrating member may be moved away from the penetrating opening after the penetration.

Alternatively, there may be adopted a method in which the first and the second liquid storage portions are formed through a partition, and the partition is removed (for example, destroyed).

The liquid ejection device according to the present invention may also be preferably adapted to an inhaler with which a user performs inhalation. In this case, the inhaler is preferably constituted of a mouthpiece having an inhaling port for inhalation by the user; a housing connected to the mouthpiece; a liquid ejection portion provided in the housing, for ejecting a liquid; and a controller for controlling the liquid ejection portion. Further, it is also preferable to provide a detector (such as a negative pressure sensor) for detecting the inhalation performed by the user so that the ejection may be carried out in response to the inhalation.

Also, the use of the liquid ejection device according to the present invention is not limited to inhalation, and may also be suitably used for administrating drugs to, for example, the scalp, the skin, an eye, or an affected part (such as wound).

The liquid ejection device according to the present invention may also be used as a fragrance generator. For example, when liquids containing different fragrant components are, respectively, put in liquid storage portions, the fragrant components can be suitably combined as needed.

Further, the liquid ejection device may also be used as a cartridge for an ink jet printer, in which the first liquid storage portion stores a transparent liquid for ejection and the other liquid storage portions each contain a dye component or pigment component, thereby making it possible to mix the necessary components.

Also, in a case where the liquids need to be mixed in particular order, the plurality of liquid storage portions may be provided to be in communication with one another in series, thereby making it possible to mix the contents of the liquid storage portions at variable timings.

EMBODIMENT

Hereinafter, an embodiment of the liquid ejection cartridge according to the present invention is described in detail.

This embodiment includes four constituent elements as follows:

(1) a plurality of liquid storage portions;
(2) a film for separating the plurality of liquid storage portions from one another;
(3) a film for separating a head portion and the liquid storage portion; and
(4) a cover unit having a plurality of diaphragms each having a grooved needle.

According to this embodiment, the following two operations are sequentially performed so as to make the ejection head ready for ejection.

The first operation is to apply a pressure to a diaphragm made of a deformable material, which is provided for penetrating a film which separates the plurality of liquid storage portions from one another. By this pressure application, a needle provided with a groove for liquid supply, which is installed inside of the diaphragm, sticks in the film separating the plurality of the liquid storage portions to thereby penetrate the film, with the result that the plurality of liquids are mixed within the liquid storage portions without leaking out.

The second operation is to apply a pressure to another diaphragm made of a deformable material, which is provided for penetrating a film which separates the head from the liquid storage portion. By this pressure application, a needle provided with a groove for liquid supply, which is installed inside of the diaphragm, sticks in the film separating the head from the liquid storage portion to thereby penetrate the film, thereby deforming the diaphragm, with the result that the liquids are supplied to the head thus making the head ready for ejection.

Next, description will be made with reference to the attached drawings.

Figure 2:
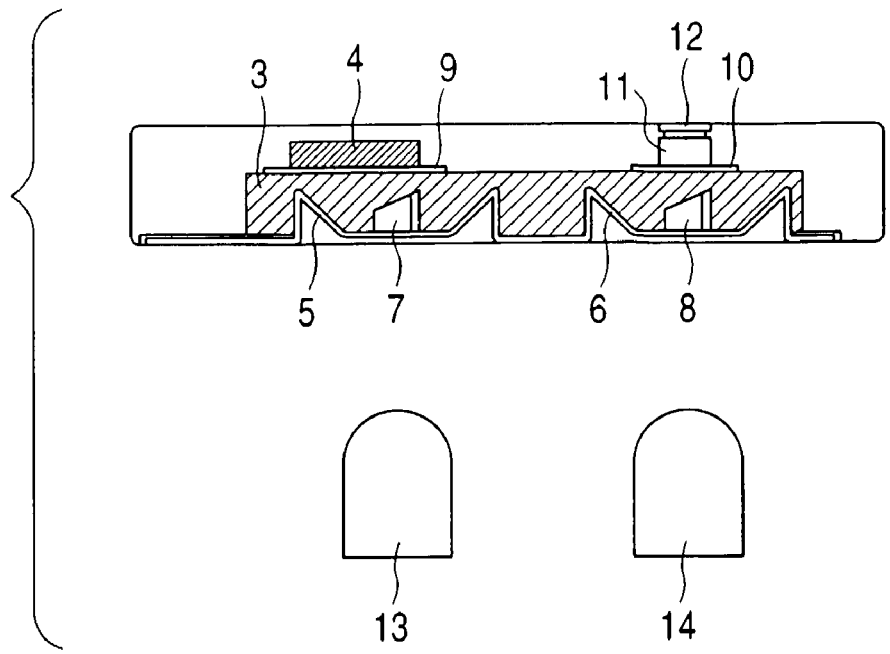
FIG. 2 is a cross-sectional view showing the liquid ejection cartridge of FIG. 1 in a state in which liquids are separately reserved in two liquid storage portions before mixing.

FIG. 1 is an exploded perspective view of a liquid ejection cartridge of the present invention, which includes four components, namely, a container unit 1, a cover unit 2, a film 9, and a film 10. FIG. 2 is a cross-sectional view of the liquid ejection cartridge.

First, explanation is made of the container unit 1. The container unit 1 includes a container 3 and a container 4 each for storing a liquid therein, each of which needs to be made of a material capable of retaining a shape independently of one another. Further, the container unit 1 also includes a flow path 11 for supplying a liquid from the container 3 to an ejection head 12.

Next, explanation is given on the cover unit 2. The cover unit includes two diaphragms 5 and 6 made of a deformable material and sharp-pointed grooved needles 7 and 8.

The grooved needles 7 and 8 each have a groove for allowing a liquid to move therethrough, and are bonded to the diaphragms 5 and 6, respectively. When a pressure is applied to the diaphragm 5, the diaphragm 5 deforms, and at the same time, the grooved needle 7 slides to penetrate the film 9, whereby the plurality of liquids are mixed through the groove. Next, when a pressure is applied to the diaphragm 6, the diaphragm 6 deforms, and at the same time, the grooved needle 8 slides to penetrate the film 10, so that the content of the diaphragm 6 is supplied the flow path 11 and the ejection head 12, thereby making the ejection head 12 ready for ejection. Moreover, the groove of the grooved needle is provided in the longitudinal direction in the side surface of a sharp-pointed cylinder, which makes it possible to supply a liquid even if the needle remains stuck in the film after being pressurized to penetrate the film.

Next, explanation is given on the films 9 and 10. The film 9 is used for sealing the container 4 so that a liquid or the like filling the container 4 does not leak out. Further, the film 10 is used for sealing so as to prevent leakage of a liquid or the like to the flow path 11 side during storage. The films 9 and 10 each may be made of a material capable of being easily penetrated by the grooved needles 7 or 8 and capable of being bonded or welded to the material of the container unit 1, and may be a resin film, or a composite film made of metal foil, paper, and the like.

(1) Formation of Tank

The container 4 in the container unit 1 is filled with a liquid or the like and sealed with the film 9 through bonding, welding, or the like. Also, the flow path 11 is sealed with the film 10. After the sealing is completed with film 9 and the film 10, the container 3 in the container unit 1 is newly filled with a liquid, and the cover unit 2 and the container unit 1 are sealed through bonding, welding, or the like thereby to form a tank.

(2) Mixing of Liquids

Figure 3:
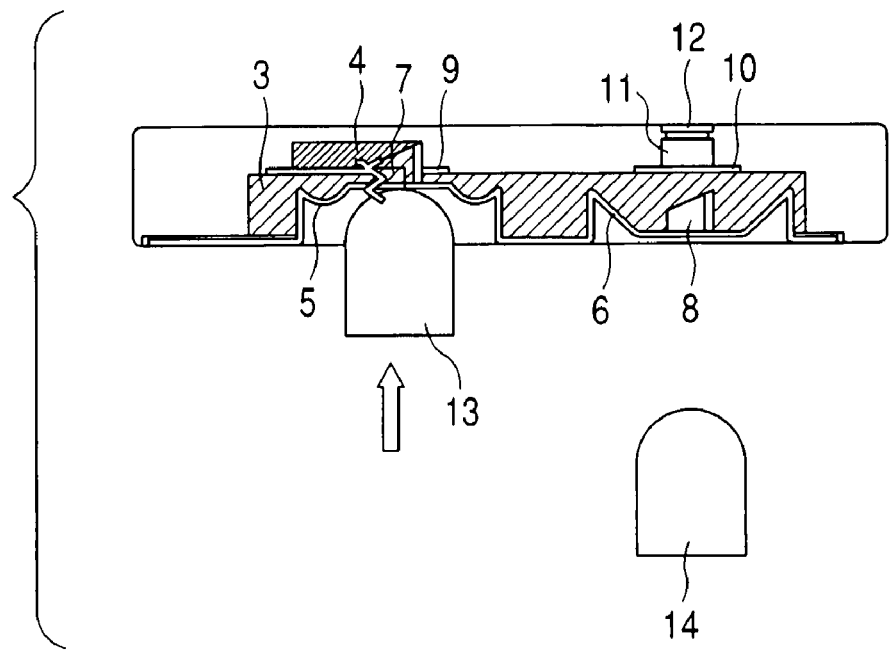
FIG. 3 is a cross-sectional view showing the liquid ejection cartridge of FIG. 1 in a state in which the liquids that have been separately reserved in the two liquid storage portions are mixed.

FIG. 3 is a cross-sectional view illustrating the liquid ejection cartridge of the present invention in a state where the liquids that have been separately reserved in the two liquid storage portions are mixed. A member 13 provided in the liquid ejection device main body for driving the cartridge is pressed against the diaphragm 5, causing the grooved needle 7 to stick and penetrate the film 9 which seals the container 4, with the result that liquids or the like in the container 3 and the container 4 are mixed within the communicating containers without leaking out. In FIG. 3, an explanation is given on a state where the member 13 is provided in the liquid ejection device main body side, while it is also possible to provide the member 13 on the mixing tank side.

Also, as the material of the diaphragm 5 and the diaphragm 6, there is preferably included a flexible material that can be deformed when pressed with a finger. The material also needs to have a shape retaining property. Examples of such material include a single component resin such as polyethylene, flexible polypropylene, polycarbonate, ABS resin, or methacrylate resin; or a composite plastic such as polyethylene/eval (trade name of ethylene vinyl alcohol copolymer; manufactured by KURARAY CO., LTD.). Also, the material of the film depends on the properties of the substance to be contained in the container.

Further, it is also possible to provide the device with a means for providing mixing or vibration in order to ensure more uniform mixing, and the device may be vibrated before ejection as needed.

(3) Supply of Liquid to Liquid Ejection Head and Preparations for Ejection

Figure 4:
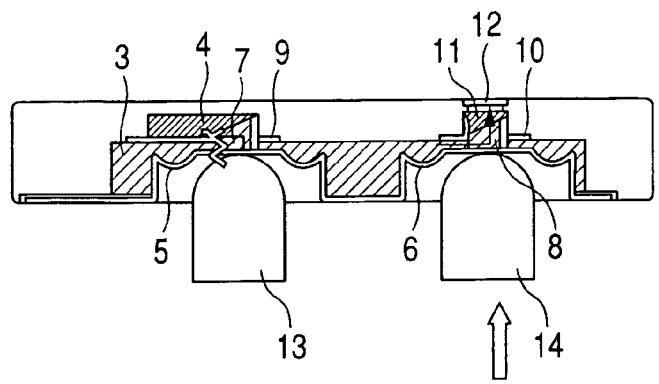
FIG. 4 is a cross-sectional view showing the liquid ejection cartridge of FIG. 1 in a state in which the mixed liquids are supplied to a liquid ejection portion.

FIG. 4 is a cross-sectional view illustrating the liquid ejection cartridge of the present invention in a state where the mixed liquids are supplied to the liquid ejection portion, and a schematic view of a structure in which the container 3, the flow path 11, and the liquid ejection head 12 are interpenetrated after the plurality of liquids have been mixed. The main body projection 14 installed in the main body applies a pressure to the diaphragm 6, causing the grooved needle 8 to stick in and penetrate the film 10 which seals the container 3, and the flow path 11 and the ejection head 12. At the same time, the diaphragm 6 deforms, with the result that the liquids are supplied to the flow path 11 and to the liquid ejection head 12, making the liquid ejection head 12 ready for ejection.

Figure 5:
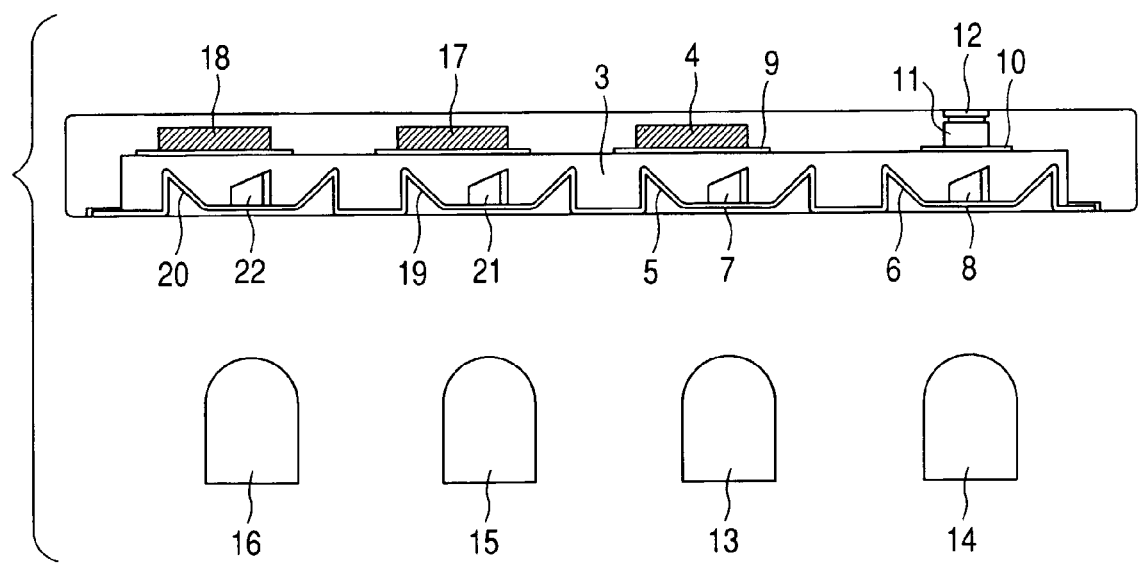
FIG. 5 is a cross-sectional view showing a liquid ejection cartridge of another embodiment of the present invention having four liquid storage portions.

FIG. 5 is a cross-sectional view of a liquid ejection cartridge having four containers. Reference numeral 17 denotes a third container; 19 denotes a third diaphragm; 21 denotes a third grooved needle; 18 denotes a fourth container; 20 denotes a fourth diaphragm; and 22 denotes a fourth grooved needle. The containers are brought into communication with one another using members 15 and 16 through the same mechanism as described above. In this case, when the liquids are contained in the containers at different concentrations, it is possible to eject liquids at a variety of concentrations, as needed. For example, when the containers, respectively, contain liquids at the concentrations shown in Table 1, it is possible to provide liquid mixtures in concentrations of six patterns shown in Table 2. Further, the components and concentrations of the liquid mixtures are not limited thereto, and may be selected appropriately depending on the need for the kinds and concentrations of the liquids, combination of liquid(s) and powder(s), and the like.

TABLE 1

| Container No. | Liquid concentration | Volume |
| --- | --- | --- |
| Container 3 | c | V |
| Container 4 | 3c | V |
| Container 17 | 5c | V |
| Container 18 | 7c | V |

TABLE 2

| Container No. | Liquid concentration | Volume |
| --- | --- | --- |
| Container 3 alone | c | V |
| Containers 3 and 4 | 2c | 2V |
| Containers 3 and 17 | 3c | 2V |
| Containers 3, 4, and 18 | (11/3)c | 3V |
| Containers 3, 4, 17, and 18 | 4c | 4V |
| Containers 3, 17, and 18 | (13/3)c | 3V |

According to the cartridge of this embodiment, the containers are brought into communication with one another to thereby mix the liquids. Accordingly, the cartridge may be easily constructed so as not to be exposed to the ambient air, which eliminates the need to provide a dust filter or the like to remove dust entering from the ambient air. Further, leakage of a liquid is also prevented, so that mixing of liquids can easily be carried out without soiling the hands.

Further, merely defining the amounts of materials in the respective containers makes it possible to control the mixing ratio, so that ejection liquids mixed at a stable ratio can be supplied to the liquid ejection portion.

Next, an explanation is given on the mechanism for applying a pressure to the diaphragm (i.e., the mechanism relating to the members 13, 14, 15, and 16 shown in FIGS. 2 to 5).

Figure 6:
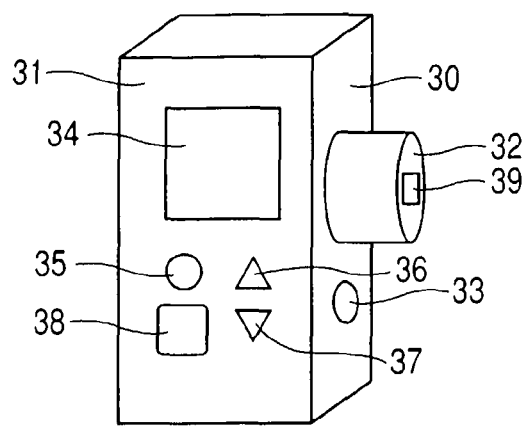
FIG. 6 is a perspective view showing an external appearance of an inhaler having a liquid ejection cartridge in accordance with an embodiment of the present invention.

FIG. 6 is a perspective view showing an external appearance of an inhaler having a liquid ejection cartridge in accordance with an embodiment of the present invention. Reference numerals 30 and 31, respectively, denote a housing case and an access cover, which constitute a main body package. Reference numeral 33 denotes an access cover lock release button for controlling the access cover 31 so as not to open during atomization of a liquid drug. The access cover 31 is provided with a display unit 34 for displaying the dose of administration, time, an error indication, and the like. There are also provided a menu setting button 35 to be used by a user for making settings; and an up button 36, a down button 37, and a determination button 38 each serving as a setting button. In a mouthpiece 32, there is provided an inhalation flow path 39 through which liquid droplets ejected from the liquid ejection cartridge are carried by an inhalation air flow.

Figure 7:
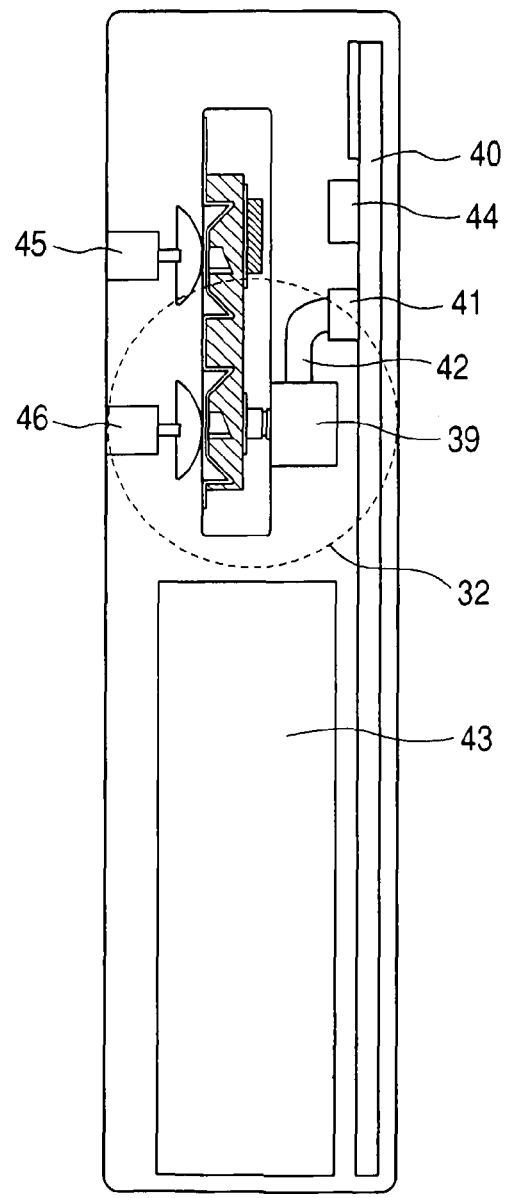
FIG. 7 is a cross-sectional view illustrating liquid mixing in the inhaler of FIG. 6.

FIG. 7 is a cross-sectional view illustrating liquid mixing in the inhaler of FIG. 6. For efficient inhalation of a liquid drug, it is preferable that the ejection of the liquid drug is synchronized with the inhalation of the user. In order to establish the synchronization, it is preferable that the inhalation performed by the user is detected and the ejection is started based on an inhalation detection signal. As an inhalation detection sensor, a negative pressure sensor 41 is provided on a control substrate 40. The negative pressure sensor 41 is in communication with the inhalation flow path 39 through a communicating tube 42.

On the control substrate 40, an inclination detection sensor 44 of a 3-axis acceleration system is installed and is used for correction for increasing the accuracy in measuring the remaining amount of the liquid drug and also for allowing the user to perform inhalation at a good orientation of the device. The inclination detection sensor 44 detects an abnormal orientation of the inhaler, and the detection result is preferably notified to the user by being displayed on the display unit 34 provided on the access cover 31 with being accompanied by a sound, a vibration generated by a vibration motor, or illumination through an LED or the like. Further, on the control substrate 40, there are provided at least a RAM and a flash ROM for storing prescription data or the like; a ROM for storing an operation program for the inhaler; and a CPU for controlling the inhaler based on the data stored in the ROM and the RAM.

The access cover 31 is opened and the liquid ejection cartridge is installed. In this embodiment, the access cover 31 is provided with a mixing actuator 45 and a supply actuator 46 on the backside thereof. The access cover 31 is closed and locked to operate the mixing actuator 45. The mixing actuator 45 performs the first operation described above to mix the plurality of liquids. Then, the supply actuator 46 is operated and performs the second operation described above to supply the liquids so as to make the liquids ready to be ejected. Incidentally, reference numeral 43 employed in FIG. 7 denotes a power source such as a battery.

Figure 8:
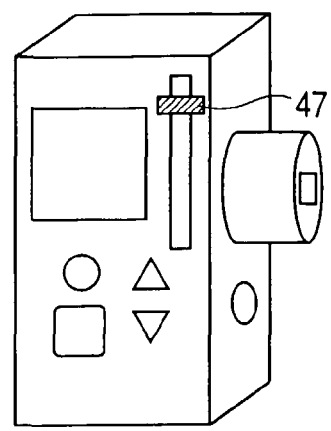
FIG. 8 is a perspective view showing an external appearance of an inhaler having a liquid ejection cartridge in accordance with another embodiment of the present invention.

FIG. 8 is a perspective view showing an external appearance of an inhaler having a liquid ejection cartridge in accordance with another embodiment of the present invention. As explained below, the inhaler may have a structure in which the liquids are mixed by the user before inhalation with the use of a sliding bar mounted on the inhaler. A slider 47 is mounted to the access cover 31. After the liquid ejection cartridge is installed and the access cover 31 is closed, the slider 47 is slid.

Figure 9:
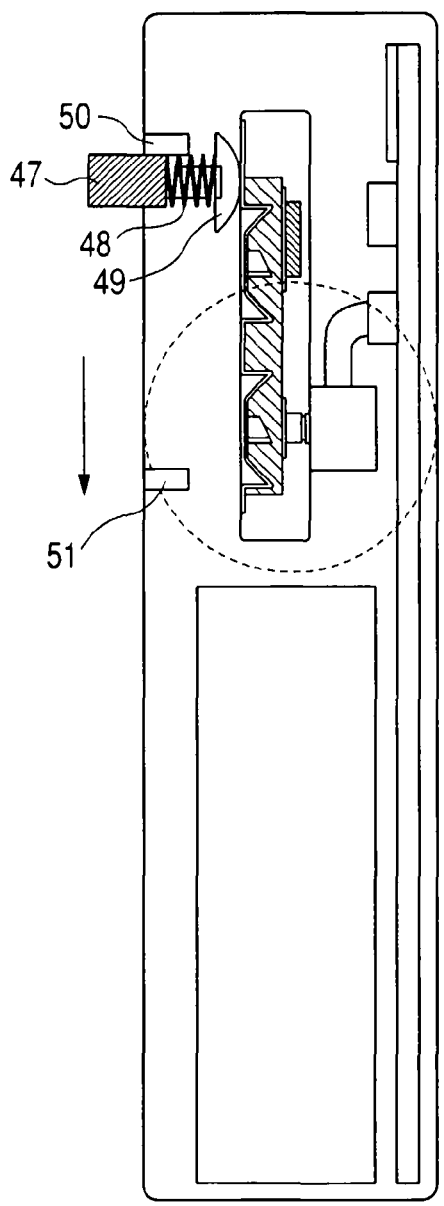
FIG. 9 is a cross-sectional view illustrating liquid mixing in the inhaler of FIG. 8.

FIG. 9 is a cross-sectional view illustrating liquid mixing in the inhaler of FIG. 8. As shown in FIG. 9, the slider 47 is provided with a diaphragm pressing portion 49 and a compressed spring 48. When the slider 47 is slid in the direction indicated by the solid arrow, the diaphragm pressing portion 49 presses the diaphragm 5 and the diaphragm 6 in the mentioned order, and is stopped by a stopper 51 provided at the lower end, making the liquid drugs ready to be ejected. After completion of the ejection, the slider 47 is brought back to a stopper 50 provided at the upper end. With this mechanism, it is possible to perform the mixing of the liquids and the filling of the ejection head with the mixed liquids, through one operation.

As described above, the mechanism for applying a pressure to the diaphragm may take various forms, and is not limited to this embodiment. Also, without employing the pressing mechanisms provided in the inhaler, the user may press the diaphragm by his finger to mix the liquids prior to installation.

The present invention is not limited to the above embodiments and various changes and modifications can be made within the spirit and scope of the present invention. Therefore to apprise the public of the scope of the present invention, the following claims are made.

This application claims priority from Japanese Patent Application No. 2005-303179 filed Oct. 18, 2005, which is hereby incorporated by reference herein.

The invention claims:

1. A liquid ejection cartridge, comprising:

a liquid ejection portion for ejecting a liquid;

a first liquid storage portion which is separated from said liquid ejection portion through a film;

a second liquid storage portion which is separated from said first liquid storage portion through a film;

a first penetrating member for penetrating said film which separates said liquid ejection portion and said first liquid storage portion; and a second penetrating member for penetrating said film which separates said first liquid storage portion and said second liquid storage portion, wherein said first penetrating member and said second penetrating member are provided in said first liquid storage portion, and wherein said liquid ejection portion is an ink jet head.

2. The liquid ejection cartridge according to claim 1, further comprising:

at least one liquid storage portion which is separated from said first liquid storage portion through a film; and at least one penetrating member for penetrating said film.

3. The liquid ejection cartridge according to claim 1, wherein the combination of the liquids contained, respectively, in said plurality of liquid storage portions is such that a state of the liquids is subjected to a change over time by mixing.

4. A liquid ejection device, comprising:

a holding portion for holding said liquid ejection cartridge set forth in claim 1; and a controlling portion for controlling said liquid ejection portion.

5. The liquid ejection device according to claim 4, further comprising:

a mechanism for moving said first penetrating member and said second penetrating member.

6. An inhaler for allowing a user to inhale a drug as liquid droplets, comprising said liquid ejection device set forth in claim 4.

7. The inhaler according to claim 6, which is so configured as to be portably carried by the user.

8. The liquid ejection cartridge according to claim 2, wherein said liquid storage portions contain liquids which have the same composition, but different concentrations.

* * * * *